US008998975B2

(12) United States Patent
Rowe

(10) Patent No.: US 8,998,975 B2
(45) Date of Patent: Apr. 7, 2015

(54) HELICAL STENT WITH ORTHOGONAL END AND METHOD OF FORMING STENT

(71) Applicant: Medtronic Vascular, Inc., Santa Rosa, CA (US)

(72) Inventor: Travis Rowe, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 6 days.

(21) Appl. No.: 13/674,438

(22) Filed: Nov. 12, 2012

(65) Prior Publication Data

US 2014/0135904 A1    May 15, 2014

(51) Int. Cl.
*A61F 2/88* (2006.01)
*A61F 2/89* (2013.01)

(52) U.S. Cl.
CPC ... *A61F 2/88* (2013.01); *A61F 2/89* (2013.01); *A61F 2220/0041* (2013.01); *A61F 2240/002* (2013.01); *A61F 2250/0007* (2013.01)

(58) Field of Classification Search
CPC .............. A61F 2/04; A61F 2/06; A61F 2/07; A61F 2/82; A61F 2/2427; A61F 2002/828
USPC ............................... 623/1.11–1.54
See application file for complete search history.

(56) References Cited

U.S. PATENT DOCUMENTS

| 4,886,062 A | 12/1989 | Wiktor |
| 5,314,472 A * | 5/1994 | Fontaine ....................... 623/1.22 |
| 2004/0117004 A1* | 6/2004 | Osborne et al. .............. 623/1.36 |
| 2008/0319534 A1* | 12/2008 | Birdsall et al. ............... 623/1.22 |

FOREIGN PATENT DOCUMENTS

| WO | WO96/41592 | 12/1996 |
| WO | WO2005/013854 | 2/2005 |
| WO | WO2010/027494 | 3/2010 |

OTHER PUBLICATIONS

PCT/US2013/068344 PCT International Search Report, mailed May 9, 2014.

* cited by examiner

*Primary Examiner* — David Isabella
*Assistant Examiner* — Ann Schillinger

(57) ABSTRACT

A helical stent includes a central segment having a first tubular waveform and a first end segment having a second tubular waveform. The waveforms are defined by a plurality of struts and a plurality of crowns connecting adjacent struts together. The struts of the second tubular waveform have different lengths such that second tubular waveform includes a plurality of amplitudes. The second tubular waveform comprises a complete turn around a longitudinal axis of the stent. A first connector connects together the first tubular waveform first end, the second tubular waveform first end, and the second tubular waveform second end. Due to the configuration of the second tubular waveform of the first end segment, the stent end at the first end segment is substantially orthogonal to the longitudinal axis of the stent. A second end segment similar to the first end segment can be connected to a second end of the first tubular waveform.

7 Claims, 5 Drawing Sheets

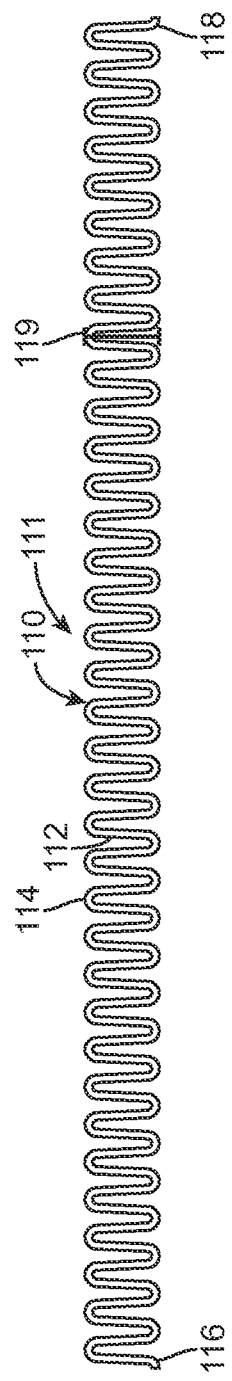
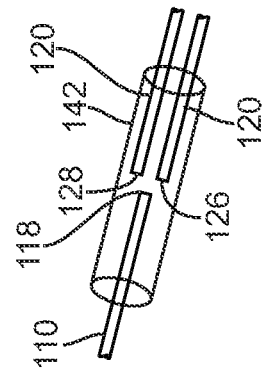
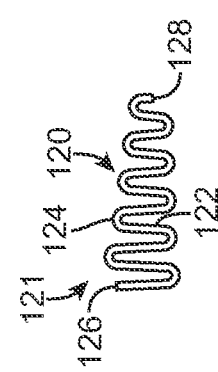
FIG. 2
FIG. 3
FIG. 4
FIG. 5

HELICAL STENT WITH ORTHOGONAL END AND METHOD OF FORMING STENT

FIELD OF THE INVENTION

The present invention relates to a helical stent formed from a waveform and having an end that is orthogonal relative to a longitudinal axis of the stent, and to a method of manufacturing a stent having a waveform and an end that is orthogonal to the longitudinal axis of the stent.

BACKGROUND

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a delivery system that includes a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter. Similarly, a self-expanding stent is formed from a memory shape material that tends to return to its radially expanded configuration. The stent is crimped into a radially compressed configuration within a sleeve of a delivery catheter. After delivery to the treatment site, the sleeve is withdrawn such that the stent is permitted to expand to its radially expanded configuration.

Stents may be formed from wire(s), may be cut from a tube, or may be cut from a sheet of material and then rolled into a tube-like structure. Stents cut from a tube or from a sheet of material normally are oriented substantially perpendicular to a longitudinal axis of the stent. Similarly, some stents formed from wires have the wires formed into a plurality of rings that are aligned parallel to each other and connected to each, and are also oriented substantially perpendicular to the longitudinal axis of the stent. Helically wound stents may be formed by helically wrapping a wire around a mandrel with pins disposed thereon. The pattern of the pins on the mandrel determines the shape of the tubular waveform formed. Helically wound stents, such as those described in U.S. Pat. No. 4,886,062 to Wiktor, the contents of which are incorporated herein by reference, may also be formed by forming a wire into a waveform, such as a sinusoid, that is then helically wrapped around a mandrel to provide a tubular or cylindrical structure. Helically wound stents, however, generally include ends that are not substantially perpendicular to the longitudinal axis of the stent. In other words, due to the helical winding of the waveform, a portion of each end of the stent extends further longitudinally than the remainder of each end of the stent, as shown in FIG. 2 of the Wiktor patent.

In some helically wound stents, such as those described in U.S. Pat. No. 5,314,472 to Fontaine, end portions of the wire have a reduced amplitude waveform as compared to the waveforms in the middle of the wire. Wrapping such a wire around a mandrel to form a stent may result in a stent with ends that may be generally perpendicular to the longitudinal axis of the stent.

However, these types of stents with end segments with a different waveform than the central segment of the stent may be inefficient to manufacture. For example, if a single wire is used, the waveform must be changed at least once (normally twice as each end segment normally has the waveform variation). For example, the waveform for a first end segment is started on the wire, then the waveform is changed to the waveform for the central segment, then the waveform must again be changed for the second end segment. Further, the waveforms for each stent must essentially be individually made, either by using only a length of wire for the stent, or by creating several waveforms in a wire in the order necessary to make each individual stent. In other methods, the end segments are made separate from the central segment and attached thereto. However, using these methods, the ends of the central segment and ends segments may be raw ends that could potentially damage the vessel into which the stent is to be implanted, or parts of the catheter used to deliver the stent.

Accordingly, it would be desirable to be able to create the waveform for the central segment of the stent in bulk. Similarly, it would be desirable to make the waveform for the end segments in bulk. Then, when it is desired to make a stent of a given length, the bulk central waveform can be cut to the appropriate length, and joined to the end segment waveforms in a manner that provides ends that are substantially orthogonal to the longitudinal axis of the stent and without exposed raw ends of the wires.

SUMMARY OF THE INVENTION

Embodiments hereof relate to a helically wrapped stent including a central segment having a first waveform and a first end segment having a second waveform. The waveforms are defined by a plurality of struts and a plurality of crowns connecting adjacent struts together. The first waveform is wrapped around a longitudinal axis of the stent at a pitch to define a plurality of helical turns. The first waveform includes a first waveform first end and a first waveform second end. The second waveform includes plurality of struts having different lengths such that second waveform includes a plurality of amplitudes. The second waveform includes a second waveform first end and a second waveform second end. The second waveform is helically wrapped around a longitudinal axis of the stent one complete turn. A first connector connects together the first waveform first end, the second waveform first end, and the second waveform second end. Due to the waveform of the first end segment, the stent end at the first end segment is substantially orthogonal to the longitudinal axis of the stent.

A third waveform may be connected to the first waveform second end. Similar to the second waveform, the third waveform is defined by a plurality of struts and a plurality of crowns connecting adjacent struts together. The struts of the third waveform vary in length to form a plurality of amplitudes. The third waveform is helically wrapped around the longitudinal axis of the stent one complete turn. A second connector connects together the first waveform second end, the third waveform first end, and the third waveform second end. Due to the waveform of the second end segment, the stent end at the second end segment is substantially orthogonal to the longitudinal axis of the stent.

Embodiments hereof also relate to a method of making a stent. The method includes the step of forming a first tubular waveform. The first tubular waveform includes a plurality of struts and a plurality of crowns connecting adjacent struts together. The first tubular waveform includes a first tubular waveform first end and a first tubular waveform second end. The method further includes the step of forming a second tubular waveform. The second tubular waveform includes a plurality of struts and a plurality of crowns connecting adjacent struts together, the plurality of struts having different lengths such that second waveform includes a plurality of amplitudes. The second tubular waveform is formed by helically wrapping a second wire around a mandrel and around pins disposed on the mandrel. The pins are disposed on the mandrel in the desired pattern of the second tubular waveform. The second tubular waveform is heat treated to set the shape of the second tubular waveform. The second tubular waveform may be formed as one complete turn around the circumference of the mandrel or may may be formed with several turns and cut to one complete turn such that the second tubular waveform includes a second tubular waveform first end and a second tubular waveform second end. The first tubular waveform first end is connected to the second tubular waveform first end and to the second tubular waveform second end.

The method may include the step of forming a third tubular waveform. The third tubular waveform may be formed in the same manner of the second tubular waveform. The third tubular waveform may be a complete turn cut from the second tubular waveform. The third tubular waveform includes a plurality of struts and a plurality of crowns connecting adjacent struts together, the plurality of struts having different lengths such that third tubular waveform includes a plurality of amplitudes. The third tubular waveform includes a third tubular waveform first end and a third tubular waveform second end. The first tubular waveform second end is connected to the third tubular waveform first end and to the third tubular waveform second end.

BRIEF DESCRIPTION OF DRAWINGS

FIG. 2 is schematic diagram of a waveform for a central segment of the stent of FIG. 1 shown cut and flattened.

FIG. 3 is a schematic diagram of a waveform for a first end segment of the stent of FIG. 1 shown cut and flattened.

FIG. 4 is a schematic diagram of a waveform in a flattened view for a second end segment of the stent of FIG. 1 shown cut and flattened.

FIG. 5 is a schematic diagram showing a connector connecting an end of the central segment and both ends of one of the end segments of the stent of FIG. 1.

DETAILED DESCRIPTION

Specific embodiments of the present invention are now described with reference to the figures, wherein like reference numbers indicate identical or functionally similar elements. The term "self-expanding" is used in the following description with reference to one or more stent structures of the prostheses hereof and is intended to convey that the structures are shaped or formed from a material that can be provided with a mechanical memory to return the structure from a compressed or constricted delivery configuration to an expanded deployed configuration. Non-exhaustive exemplary self-expanding materials include stainless steel, a pseudo-elastic metal such as a nickel titanium alloy or nitinol, various polymers, or a so-called super alloy, which may have a base metal of nickel, cobalt, chromium, or other metal. Mechanical memory may be imparted to a wire or stent structure by thermal treatment to achieve a spring temper in stainless steel, for example, or to set a shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprylactone copolymer and poly cyclo-octine can be used separately or in conjunction with other shape memory polymers.

The following detailed description is merely exemplary in nature and is not intended to limit the invention or the application and uses of the invention. Further, there is no intention to be bound by any expressed or implied theory presented in the preceding technical field, background, brief summary or the following detailed description. Still further, the drawings are not drawn to scale.

Figure 1:
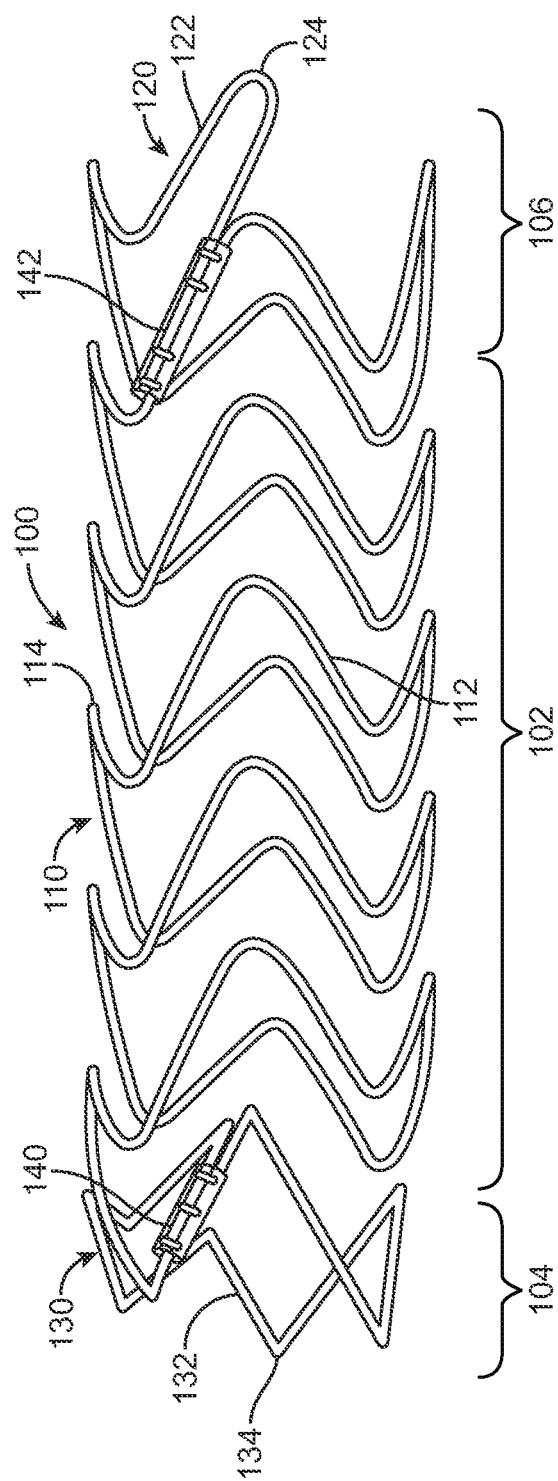
FIG. 1 is schematic perspective view of a stent according to an embodiment hereof.

FIG. 1 is a schematic perspective illustration of an exemplary stent 100 according to an embodiment hereof. Stent 100 is a helical stent. In particular, stent 100 is formed from wires helically wrapped around in a tubular waveform shape around a longitudinal axis to form the stent. The terms "filament" and "wire" as used herein mean any elongated filament or group of filaments. The filament or wire may be made of any material, such as titanium, tantalum, gold, copper or copper alloys, nickel-titanium alloys, combinations of these materials, or any other biologically compatible material used in stents as known to those skilled in the art. In a non-limiting example, the wires described herein are made from nitinol such that stent 100 is a self-expanding stent. Stent 100 includes a first end portion or segment 104, a second end portion or segment 106, and a middle or central portion or segment 102 disposed between the first and second end segments 104, 106. As shown in FIG. 1, a first crimp connector 140 connects central segment 102 to first end segment 104 and a second crimp connector 142 connects central segment 102 to second end segment 106.

As shown in FIGS. 1 and 2, central segment 102 is formed from a wire 110. Wire 110 is formed into a tubular waveform 111 including a series of straight segments or struts 112 interconnected by bends or crowns 114. In the embodiment illustrated in FIG. 2, tubular waveform 111 is shown flattened and is substantially a sinusoid having amplitude 119. However, as would be understood by those skilled in the art, other waveforms may be utilized. Further, the amplitude 119 need not be a constant amplitude as shown in FIG. 2. For example, and not by way of limitation, the length of struts 112 can be alternated between a short strut and a long strut. Accordingly, the amplitude of such a waveform would alternate between a larger amplitude and a smaller amplitude. Although the struts lengths may be varied, it is preferable that the waveform 111 have a repeating pattern so that it may be manufactured in bulk. Tubular waveform 111 formed of wire 110 includes a first end 116 and a second end 118. As utilized herein, the "end" of a wire is the longitudinal extremity of the wire.

Similarly, as shown in FIGS. 1 and 3, first end segment 104 is formed from a wire 130 formed into a tubular waveform 131. Tubular waveform 131 includes a series of struts 132 interconnected by a series of crowns 134, as known in the art. FIG. 3 shows tubular waveform 131 flattened. In the embodiment shown in FIG. 3, waveform 131 is generally sinusoidal in shape and the amplitude of the sinusoids increases from a first end 136 to a second end 138 of the waveform. However, those skilled in the art would recognize that other waveforms can be used. For example, and not by way of limitation, other shapes can be used. In a further example, and also not by way of limitation, other waveforms known in the art to provide an orthogonal end for a helically wrapped stent can be used.

Similarly, as shown in FIGS. 1 and 4, second end segment 104 is formed from a wire 120 formed into a tubular waveform 121. Waveform 121 includes a series of struts 122 interconnected by a series of crowns 124, as known in the art. FIG. 4 shows tubular waveform 121 flattened. In the embodiment shown in FIG. 4, waveform 121 is generally sinusoidal in shape and the amplitude of the sinusoids decreases from a first end 126 to a second end 128 of the waveform. However, those skilled in the art would recognize that other waveforms can be used. For example, and not by way of limitation, other shapes can be used. In a further example, and also not by way of limitation, other waveforms known in the art to provide an orthogonal end for a helically wrapped stent can be used.

FIG. 5 shows a detail of the connection between central segment 102 and second end segment 106 at crimp connector 142. In particular, second end 118 of wire 110 of central segment 102, first end 126 of wire 120 of second end segment 106, and second end 128 of wire 120 of second end segment 106 are each placed in crimp connector 142. Crimp connector 140 is then crimped together to capture second end 118 of wire 110, first end 126 of wire 120, and second end 128 of wire 120.

Figure 6:
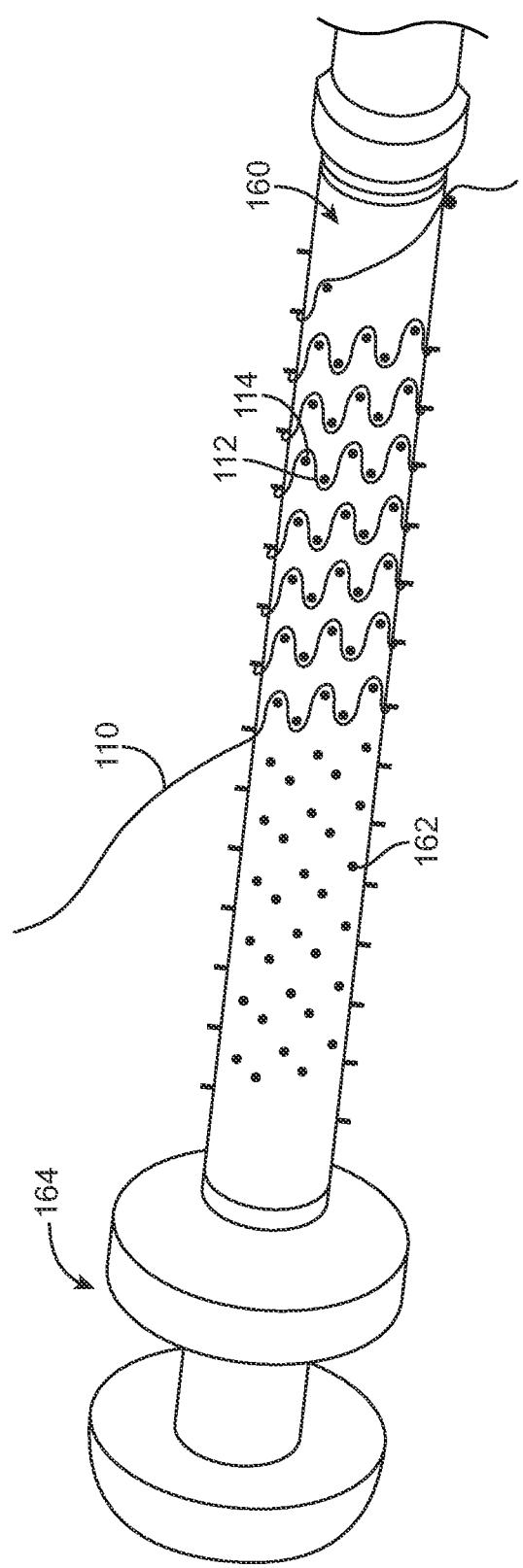
FIG. 6 is schematic diagram showing a portion of the central segment being formed on a mandrel.
Figure 7:
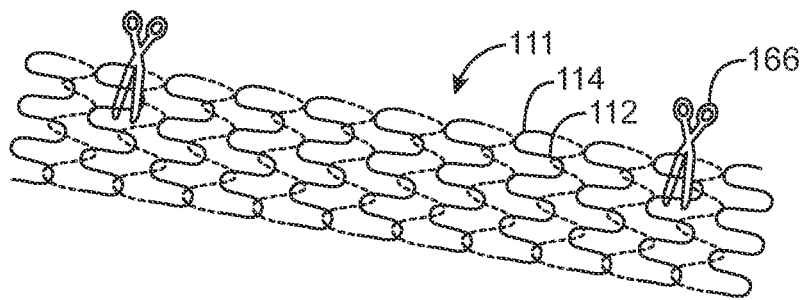
FIG. 7 is a schematic diagram show a tubular waveform in the pattern of the central segment.
Figure 8:
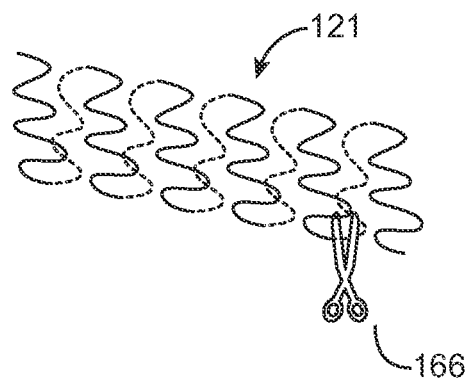
FIG. 8 is a schematic diagram showing a tubular waveform in the pattern of an end segment.
Figure 9:
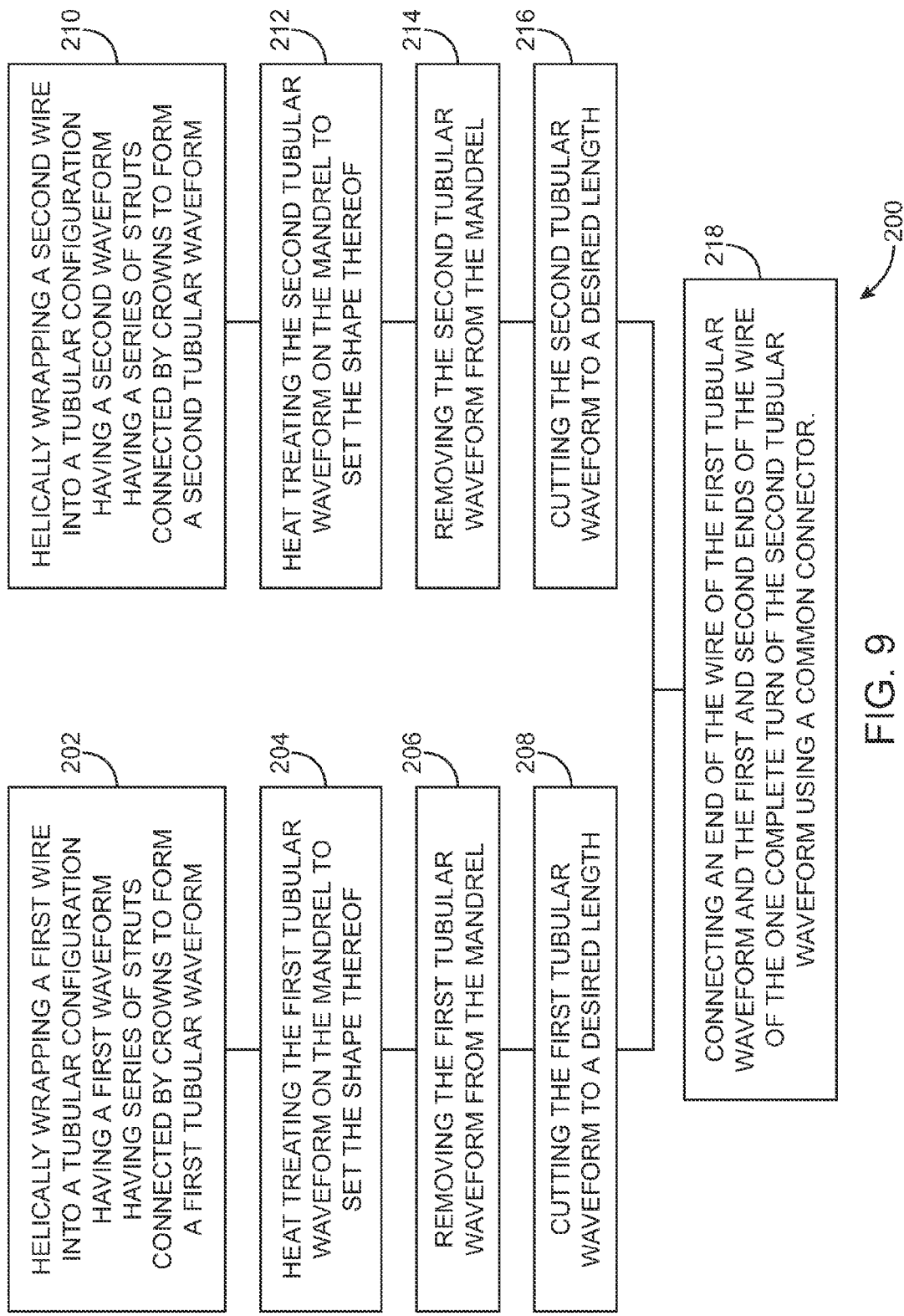
FIG. 9 is a flow chart of a method of forming the stent of FIG. 1.

FIGS. 6-9 show a method 200 of forming a stent 100 in accordance with an embodiment of the present invention. As described herein, central segment 102 and second end segment 106 are described. However, those skilled in the art would recognize that first end segment 104 would be formed and connected to central segment 102 in a similar fashion as described with respect to the second end segment 106. As shown in FIGS. 6 and 9, wire 110 is helically wrapped into a tubular configuration having a first waveform having series of struts 112 connected by crowns 114 to form a first tubular waveform 111, as described in step 202 of FIG. 9. FIG. 6 shows a particular embodiment of a method of forming first tubular waveform 111. In particular, a mandrel 160 includes pins or posts 162 on an exterior surface of mandrel 160. Wire 110 is wrapped around posts 162 to form struts 112 and crowns 114 while being helically wrapped around mandrel 160 to form into a tubular shape, as shown in FIG. 6. Wire 110 is wrapped around posts 162 and mandrel 160 by a user (not shown). Mandrel 160 may be rotated to by a motor shown generally at 164 to facilitate access to posts 162 around the circumference of mandrel 160. First tubular waveform 111 may be formed to the desired length of central segment 102. However, first tubular waveform is preferably formed in a bulk length and thereafter cut to the desired length of central segment 102, as described in more detail below.

After wire 110 is formed into first tubular waveform 111, first tubular waveform is heat treated to set the shape of first tubular waveform 111, as shown in step 204 of FIG. 9. Heat treating shape memory material such as nitinol is well known in the art. Other methods to set the shape of first tubular waveform 111 may also be used, as known to those skilled in the art. With first tubular waveform 111 set, first tubular waveform 111 may be removed from mandrel 160, as shown in step 206 of FIG. 9. First tubular waveform 111 heat set and removed from mandrel 160 is shown in FIG. 7.

If first tubular waveform 111 is formed to a length longer than the desired length of central segment 102, first tubular waveform 111 may be cut to the desired length of central segment 102, as shown in FIG. 7 and step 208 of FIG. 9. First tubular waveform 111 may be cut using a cutting tool 166 such as shears, a laser cutter, or other cutting tools known to those skilled in the art.

Similarly, second tubular waveform 121 is formed by helically wrapping wire 120 into a tubular configuration having a first waveform having a series of struts 122 connected by crowns 124, as shown in step 210 of FIG. 9. Second tubular waveform 121 may be formed in similar fashion to first tubular waveform 111. In particular, a mandrel similar to mandrel 160 of FIG. 6 may be used, except that the posts are arranged for the shape of second tubular waveform 121. In a particular non-limiting example, the posts are arranged such that for each turn around the circumference of the mandrel, the adjacent struts in the waveform would increase or decrease in length such that the amplitudes of the waveform for one complete turn would increase or decrease, as shown in the flattened waveform 121 shown in FIG. 4. Second tubular waveform 121 may be formed to the desired length of second end segment 106. However, second tubular waveform 121 is preferably formed in a bulk length and thereafter cut to the desired length of second end segment 106, as described in more detail below.

After wire 120 is formed into second tubular waveform 121, second tubular waveform 121 is heat treated to set the shape of first tubular waveform 121, as shown in step 212 of FIG. 9. Heat treating shape memory material such as nitinol is well known in the art. Other methods to set the shape of second tubular waveform 121 may also be used, as known to those skilled in the art. With the shape of second tubular waveform 121 set, second tubular waveform 121 may be removed from the mandrel, as shown in step 214 of FIG. 9. Second tubular waveform 121 heat set and removed from the mandrel is shown in FIG. 8.

If second tubular waveform 121 is formed to a length longer than the desired length of second end segment 106, second tubular waveform 121 may be cut to the desired length of second end segment 106, as shown in FIG. 8 and step 216 of FIG. 9. Second tubular waveform 121 may be cut using a cutting tool 166 such as shears, a laser cutter, or other cutting tools known to those skilled in the art.

With central segment 102 formed of first tubular waveform 111 at the desired length and second end segment 106 formed of one complete turn of second tubular waveform 121, second end 118 of wire 110 of central segment 102 is disposed adjacent first end 126 and second end 128 of wire 120 of second end segment 106. A connector, such as crimp connecter 142, connects second end 118 of wire 110 and first and second ends 126, 128 of wire 120, as shown in step 218 of FIG. 9 and in FIG. 5.

The same steps for forming second tubular waveform 121 may be used to form third tubular waveform 131. Alternatively, second tubular waveform 121 is made longer than the desired length of second end segment 106. Accordingly, first end segment 104 is formed by cutting a desired length of second tubular waveform 121. The ends of the wire of first end segment 104 are connected to the first end 116 of central segment 102 using connector 140, as described above.

Although FIGS. 6-9 described a particular method of forming stent 100, other methods known to those skilled in the art may be utilized. For example, and not by way of limitation, if the stent is to be a balloon expandable stent, the wires of each segment may be formed into the respective waveforms of FIGS. 2-4, and then helically wrapped around a mandrel. First end 116 of waveform 111 may then be connected to first and second ends 136, 138 of waveform 131 using connector 140 and/or second end 118 of waveform 111 may be connected to first and second ends 126, 128 of waveform 121.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent comprising:
   a central segment having a first tubular waveform, the first tubular waveform being defined by a plurality of struts and a plurality of crowns connecting adjacent struts together, the first tubular waveform being wrapped around a longitudinal axis of the stent at a pitch to define a plurality of helical turns, the first waveform including a first tubular waveform first end and a first tubular waveform second end;
   a first end segment connected to the first tubular waveform first end, the first end segment having a second tubular waveform that includes a plurality of struts and a plurality of crowns connecting adjacent struts together, the plurality of struts of the second tubular waveform having different lengths such that the second tubular waveform includes a plurality of amplitudes, the second tubular waveform having a second tubular waveform first end and a second tubular waveform second end which are not continuous with the first tubular waveform first end; and
   a first connector, wherein the first tubular waveform first end, the second tubular waveform first end, and the second tubular waveform second end are disposed within the first connector wherein the plurality of amplitudes of the second tubular waveform are formed such that each adjacent amplitude is larger than the preceding amplitude and smaller than the succeeding amplitude in a direction away from the central segment.

2. The stent of claim 1, wherein the connector is a crimp connector.

3. The stent of claim 1, wherein the first end segment comprises a single complete turn.

4. The stent of claim 1, further comprising:
   a second end segment connected to the first tubular waveform second end, the second end segment having a third tubular waveform that includes a plurality of struts and a plurality of crowns connecting adjacent struts together, the plurality of struts of the third tubular waveform having different lengths such that the third tubular waveform includes a plurality of amplitudes, the third tubular waveform having a third tubular waveform first end and a third tubular waveform second end which are not continuous with the first tubular waveform second end; and
   a second connector, wherein the first tubular waveform second end, the third tubular waveform first end, and the third tubular waveform second end are disposed within the second connector.

5. The stent of claim 4, wherein the plurality of amplitudes of the third tubular waveform are formed such that each adjacent amplitude is larger than the preceding amplitude and smaller than the succeeding amplitude in a direction away from the central segment.

6. The stent of claim 4, wherein the second connector is a crimp connector.

7. The stent of claim 4, wherein the second end segment comprises a single complete turn.

\* \* \* \* \*